United States Patent [19]

McKnight et al.

[11] Patent Number: 4,500,247

[45] Date of Patent: Feb. 19, 1985

[54] SYRINGE INSPECTION APPARATUS

[75] Inventors: Hugh P. McKnight, Indianapolis; Kenneth B. Welty; Harold B. Dinius, both of Mooresville, all of Ind.

[73] Assignee: Eli Lilly and Company, Indianapolis, Ind.

[21] Appl. No.: 581,423

[22] Filed: Feb. 17, 1984

Related U.S. Application Data

[62] Division of Ser. No. 373,979, May 3, 1982, Pat. No. 4,456,115.

[51] Int. Cl.³ ............................................. B65B 21/02
[52] U.S. Cl. ..................................... 414/416; 198/448
[58] Field of Search ............... 414/416, 222, 225, 749, 414/751; 198/448, 486, 456, 457, 433; 294/87 R, 93

[56] References Cited

U.S. PATENT DOCUMENTS

| 1,620,778 | 3/1927 | Odom | 198/486 X |
|---|---|---|---|
| 2,268,098 | 12/1941 | Weathers | 88/14 |
| 2,936,798 | 5/1960 | Cummings et al. | 141/88 |
| 3,548,745 | 12/1970 | Sirvet et al. | 101/40 |
| 3,651,985 | 3/1972 | Smith | 198/486 X |
| 3,701,410 | 10/1972 | Shields | 198/486 |
| 3,714,770 | 2/1973 | Rothke | 57/52 |
| 3,780,492 | 12/1973 | Corderoy | 53/247 |
| 3,844,428 | 10/1974 | Olsen | 414/222 X |
| 3,970,201 | 7/1976 | Keene | 214/309 |
| 3,990,566 | 11/1976 | Nordqvist | 198/419 |
| 4,076,113 | 2/1978 | Shields | 198/403 |
| 4,417,662 | 11/1983 | Nicholson et al. | 209/522 |

FOREIGN PATENT DOCUMENTS

| 52-61074 | 5/1977 | Japan | 414/416 |
|---|---|---|---|
| 6406307 | 12/1964 | Netherlands | 414/416 |
| 55133 | 9/1923 | Sweden | |
| 713770 | 8/1954 | United Kingdom | |

Primary Examiner—Joseph E. Valenza
Assistant Examiner—Jonathan D. Holmes
Attorney, Agent, or Firm—Barnes & Thornburg

[57] ABSTRACT

Rows of ten filled hypodermic syringes, without rods and in depending position, are transferred successively from ten-row trays to a rail conveyor by a gang chuck having ten expansible inserts which enter and lift the syringes by their open piston ends. The trays are supported by a loading table which is moved stepwise and shifted to successively align offset rows of syringes with the gang chuck.

9 Claims, 13 Drawing Figures

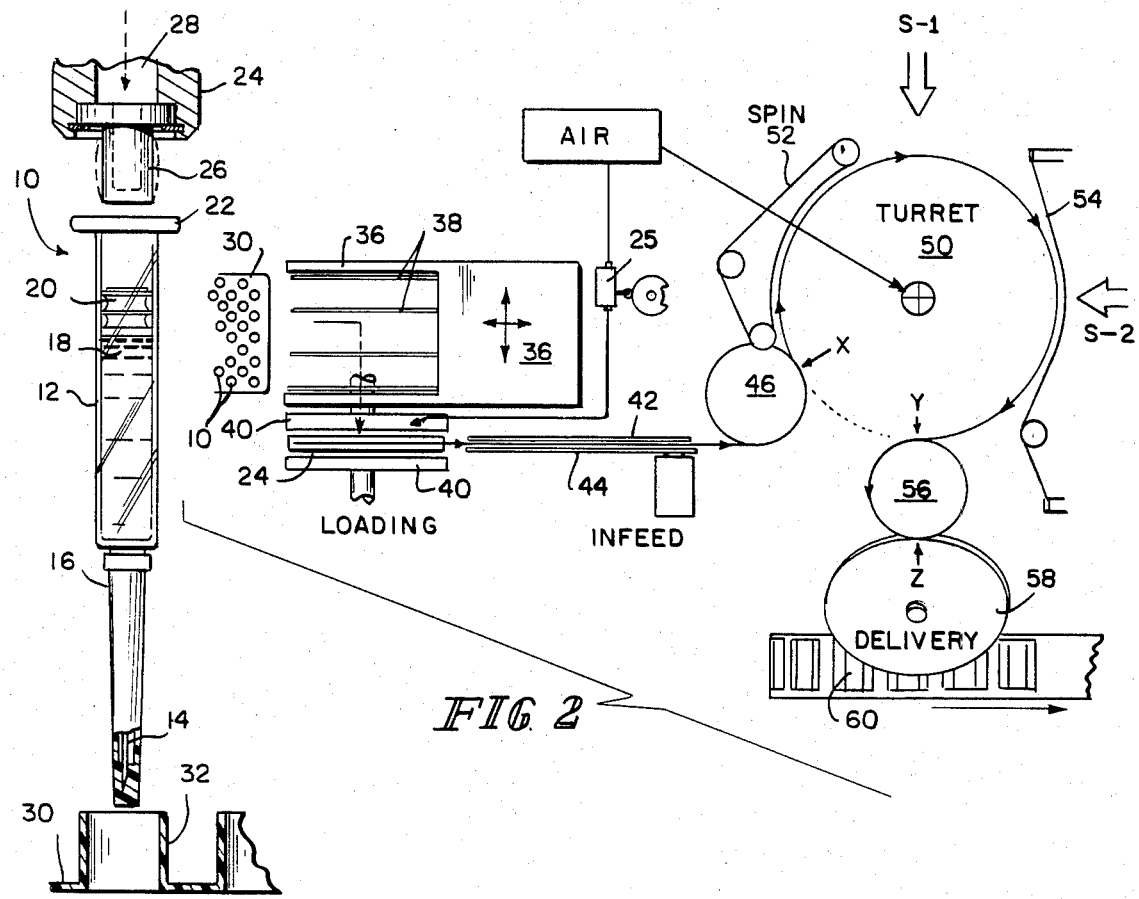
FIG. 1
FIG. 2
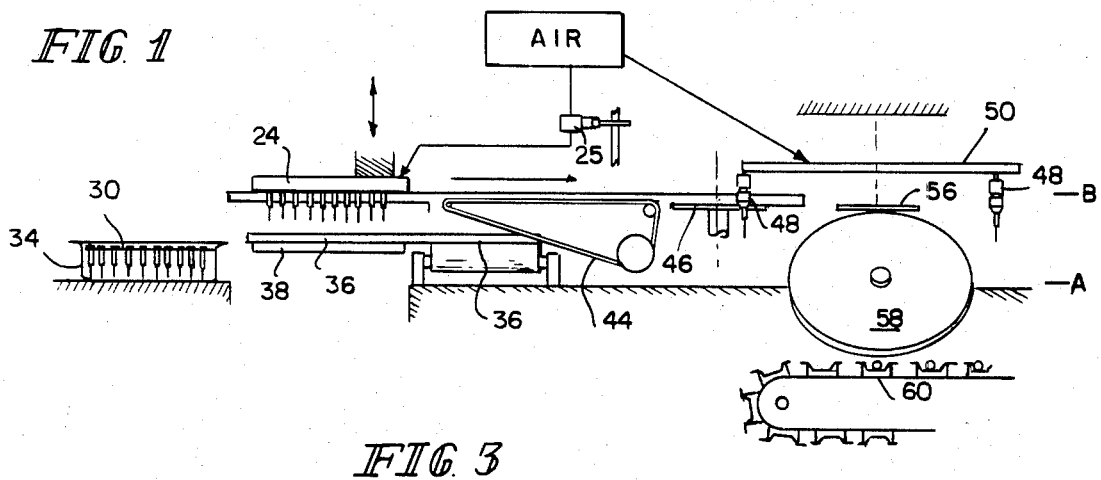
FIG. 3

SYRINGE INSPECTION APPARATUS

This is a division of application Ser. No. 373,979, filed May 3, 1982 now U.S. Pat. No. 4,456,115.

This invention relates to inspection apparatus, particularly for the inspection of filled hypodermic syringes, such as those comprising a transparent tubular body having a reduced needle end to which a needle may be attached together with a protective cap which seals and protects the needle, and having an opposite open end provided with an outward-extending finger flange for engagement by the fingers during administrative use of the syringe. The body contains a measured quantity of liquid to be administered, and is closed by a piston to which a piston rod is to be attached after inspection.

Co-pending application Ser. No. 260,003, filed May 4, 1981, by our fellow workers David W. Nicholson et al, now U.S. Pat. No. 4,417,662 and assigned to the assignee of this application, discloses apparatus for inspecting filled medicinal vials. In some respects, syringe inspection is similar to vial inspection, but the handling of filled syringes presents significantly different problems. The present application is directed to the solution of problems arising from the nature and inspection requirements of filled hypodermic syringes and to the adaptation of certain concepts from the vial inspection apparatus to the inspection of the significantly different syringes.

In one common practice, syringe bodies with needles attached and covered by a needle cap are delivered by the manufacturer in sealed boxes or "tubs" in 100-syringe lots supported by a carrier plate in ten staggered rows of ten syringes each. The carrier plate is supported near the top of the box and formed with rows of upstanding tubular collars of a size to receive the syringe bodies and to support them by their finger flanges and with their needle ends depending below the carrier. The tubs also include an upper stopper-carrier which contains stoppers in position to be pushed downward into the syringes after they are filled. In filling, the stopper carrier is removed and the entire tub of 100 syringes is inserted in a filling machine where the syringes are filled. The stopper carrier is then returned to a position above the syringes, and the stoppers are inserted in the syringes under vacuum.

The inspection apparatus of the present invention is adapted to be loaded directly from the carrier plates containing 100-syringe lots of filled syringes arranged in ten staggered rows of ten syringes each.

In accordance with the invention, syringe carrier plates supporting ten rows of ten syringes each are manually loaded on a loading table of the inspection apparatus, positioned in a starting position. The load carrier is moved, stepwise, to present the successive rows of syringes to a vertically movable gang chuck fitted with ten expansible inserts. Such inserts are engaged in the open upper ends of the syringe bodies and expanded to clutch the bodies to the chuck, and the gang chuck is then raised to position the ten syringes between rails of a rail conveyor, and the syringes are then transferred from the gang chuck to such conveyor. The conveyor feeds the line of syringes to the infeed mechanism of a turret or like carrier having a continuous series of rotatable and axially movable chucks, each having an expansible insert. The inserts of the chuck are engaged in the upper ends of the syringes and expanded, and the chucks then carry the syringes in suspended position sequentially and with continuous travel along an inspection path and past at least one, and preferably at least two, inspection stations at which the syringes are inspected in different ways.

At one inspection station, the inspection is for the presence of solid particles. For this purpose the chucks and their suspended syringes are rapidly spun on the their axes in advance, and the spinning is abruptly stopped as the syringes enter the inspection station. The liquid in the syringes continues to spin, and this causes the solid particles to remain suspended in the liquid so as to be observable during the inspection.

In accordance with the present invention, the syringes are stabilized in their spinning by a stabilizing bar extending along the inspection path and positioned to engage eccentrically spinning syringes to stabilize them for spinning on their axes. A second station may provide for inspection of the syringes for relatively gross defects, such as inadequate fill level, absent or misapplied pistons, cracked syringe bodies, etc., and for this purpose, the chucks and syringes may be caused to rotate slowly as they pass through the second inspection station. When defective syringes are noticed during either inspection, the operator manually pulls them off the inflated inserts of the chucks and drops them into a rejected chute.

After inspection, the vertically positioned syringes are transferred to an angularly disposed delivery wheel which receives the syringes in vertical position and carries them through a conical path and tilts them to a horizontal position for delivery in horizontal parallel positions. A linear conveyor may carry the thus-delivered syringes to other apparatus such as a piston rod-inserting apparatus and/or labelling and packaging apparatus.

The general character of the inspections, and the use of a turret with rotatable and axially movable chucks, is to some extent similar to that in the vial inspection apparatus of U.S. Pat. No. 4,417,662. However, syringes present substantially different problems than vials, especially with respect to loading and handling and outfeed delivery, which problems are overcome by the present invention.

The accompanying drawings illustrate the invention and show a preferred embodiment of the invention exemplifying the best mode of carrying out the invention as presently perceived. In such drawings:

FIG. 1 is a side elevation of a syringe of the type adapted to be handled and inspected with the use of the present apparatus, shown in separated relation with an upper chuck having an expandable insert and in relation with a fragmental portion of a syringe carrier plate such as that used to support syringes in tubs as delivered from the filling apparatus;

FIG. 2 is a diagrammatic plan view of inspection apparatus in accordance with the present invention;

FIG. 3 is a diagrammatic front elevation of such apparatus;

FIG. 12 is a vertical section showing the angle-delivery wheel, taken on the line 12—12 of FIG. 8.

Figure 4:
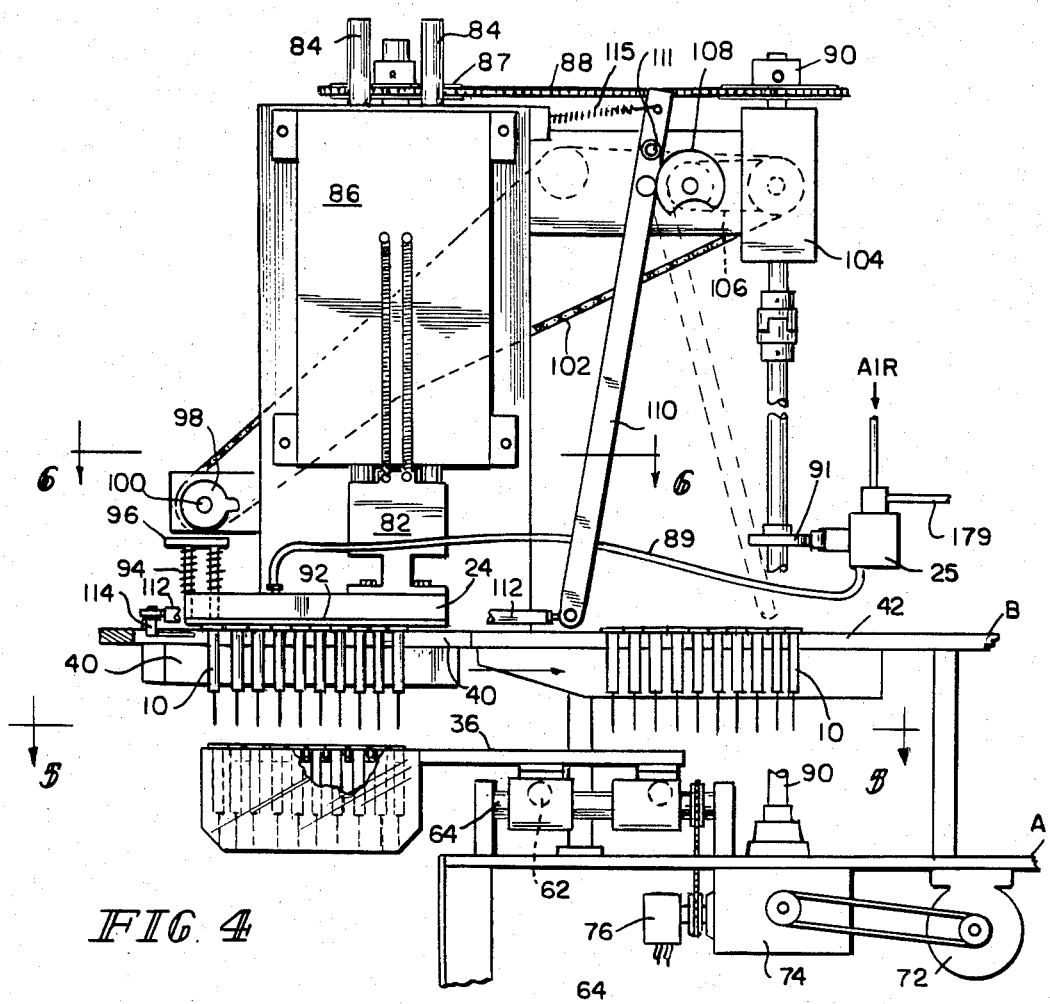
FIG. 4 is a front elevation, with parts broken away and shown in section, of the loading portion of the apparatus shown in FIGS. 3 and 4.

The syringe 10 shown in FIG. 1 comprises a tubular body 12 having a reduced lower end to which a needle 14 is attached and which carries a needle cap 16 for sealing and protecting the needle. The body 12 contains a filling of injectable liquid 18 stoppered by a piston 20 spaced a short distance below the upper open end of the body 12. The upper end of the body carries a peripheral finger flange 22 for engagement by the fingers of the user during hypodermic administration. For purposes of handling such syringes during loading, a gang chuck bar 24 carries a series of inflatable inserts 26 adapted to freely enter the open upper ends of the syringe bodies 20 and to be expanded into gripping engagement with such bodies by air pressure supplied through an air passage 28 in the chuck bar 24.

The present invention contemplates that a group of such syringes 10 will be supplied for loading into the inspection apparatus in a syringe carrier plate 30 of the type shown at the bottom of FIG. 1. This has a plurality of upstanding collars 32, each adapted to loosely receive the tubular body 12 of a syringe 10 and to engage beneath the finger flange 22 of the syringe to support the syringe in a depending vertical position.

The inspection apparatus shown diagrammatically in FIGS. 2 and 3 comprises a LOADING section, an INFEED conveyor and star wheel, a TURRET, a SPIN belt, a first inspection station S1, a second inspection station S2, a DELIVERY wheel, and an OUTFEED conveyor. For convenience, the several parts of the apparatus are mounted at four different levels designated A to D.

It is contemplated that syringes will be delivered to the inspection apparatus in 100-lot groups in tubs 34, with the syringes supported in an upper removable carrier plate 30 in ten alternately staggered rows of ten syringes each. The loading section comprises a loading table 36 having a series of support bars 38 on which a syringe carrier plate with its 100-lot syringes is manually loaded. When the operator initiates a loading cycle, the loading table 36 positions the first row of syringes 10 beneath a gang chuck 24 which stands in an elevated position above a pair of retracted conveyor rails 40. The gang chuck 24 then moves downward, between the retracted rails 40, to enter its ten inflatable inserts 26 in the upper ends of the ten syringes 10 in such first row. Air is then applied from an air valve 25 to the gang chuck to inflate such inserts to cause them to clutch the syringes, and the gang chuck 24 is then raised to a position above the conveyor rails 40, and the rails are advanced to lie alongside the bodies 12 of the syringes and beneath their upper flanges 22. The actuating air is then cut off from the gang chuck, and a stripper is actuated to ensure release of the syringes onto the rails 40. The row of syringes thus deposited on the rails 40 is then pushed forward onto the infeed conveyor. Meanwhile, the table 36 is moved transversely and jogged longitudinally to align the next row of syringes for pick-up by the gang chuck.

The infeed conveyor comprises one fixed side rail 42 and a continuously driven belt 44, which acts to advance the syringes toward the infeed star wheel 46. Such wheel feeds the syringes in spaced and timed relation to a transfer point X at which they are transferred to a series of chucks 48 on the turret 50. The chucks 48 move with the turret past a spin belt 52 which rapidly rotates the syringes as they approach the first inspection station S-1. A stabilizing bar, not here shown, stabilizes the syringes during their spinning. The chucks pass beyond the spin belt 52 so that the syringes stop spinning while the momentum of the liquid 18 in the syringes continues its rotation so as to cause solid particles therein to be suspended and observable at the inspection station. If such particles are observed in a syringe, the inspector manually pulls such syringe from the inflatable insert by which it is held on its chuck and drops it to a reject chute. The turret then carries the chucks and their suspended syringes past a second inspection station S-2, where the chucks may roll along a stationary control belt 54 which causes the chucks and the syringes to rotate slowly as they traverse the second inspection station.

The turret 50 then carries the chucks and syringes to a transfer point Y at which they are transferred to an outfeed star wheel 56, to which the chucks release their syringes for movement by such outfeed star wheel to the delivery wheel 58. This is disposed at an angle of 45° and has a conical edge face at 45° to its plane. The edge face is formed with a series of syringe-receiving pockets, which move from a vertical position at the transfer point Z of tangency with the star wheel 56 to a horizontal position 180° therefrom so as to carry the syringes from their depending vertical position at that transfer point to a horizontal delivery position at the bottom of the delivery wheel 58. The horizontal syringes are then released at that point onto an outfeed conveyor 60.

Figure 5:
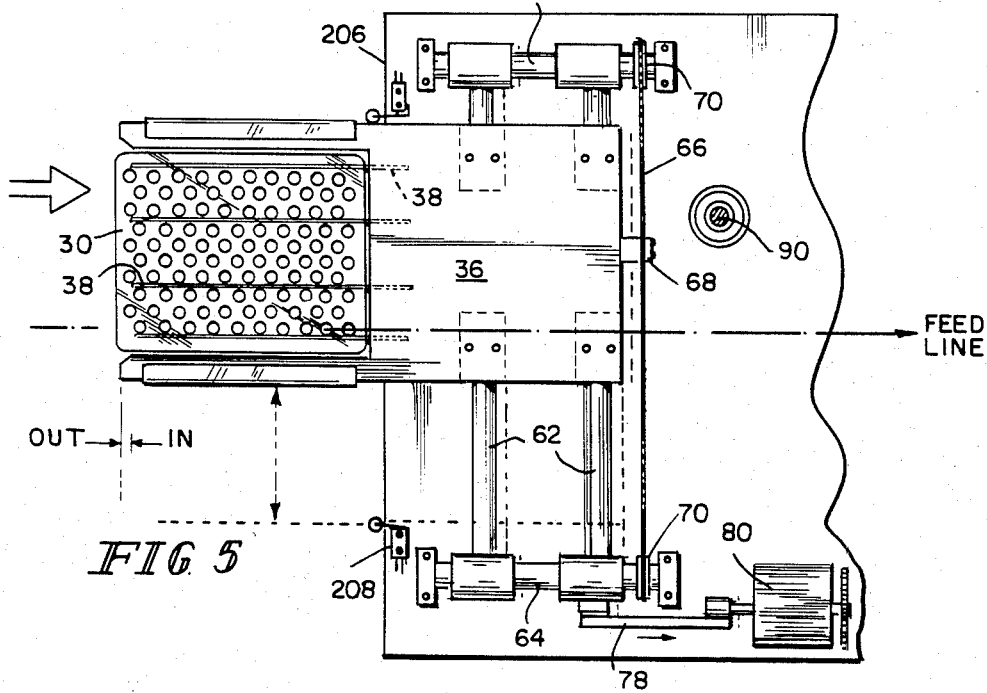
FIG. 5 is a section taken on the line 5—5 of FIG. 4, showing mechanism for feeding a 100-lot carrier of syringes to the gang chuck.
Figure 6:
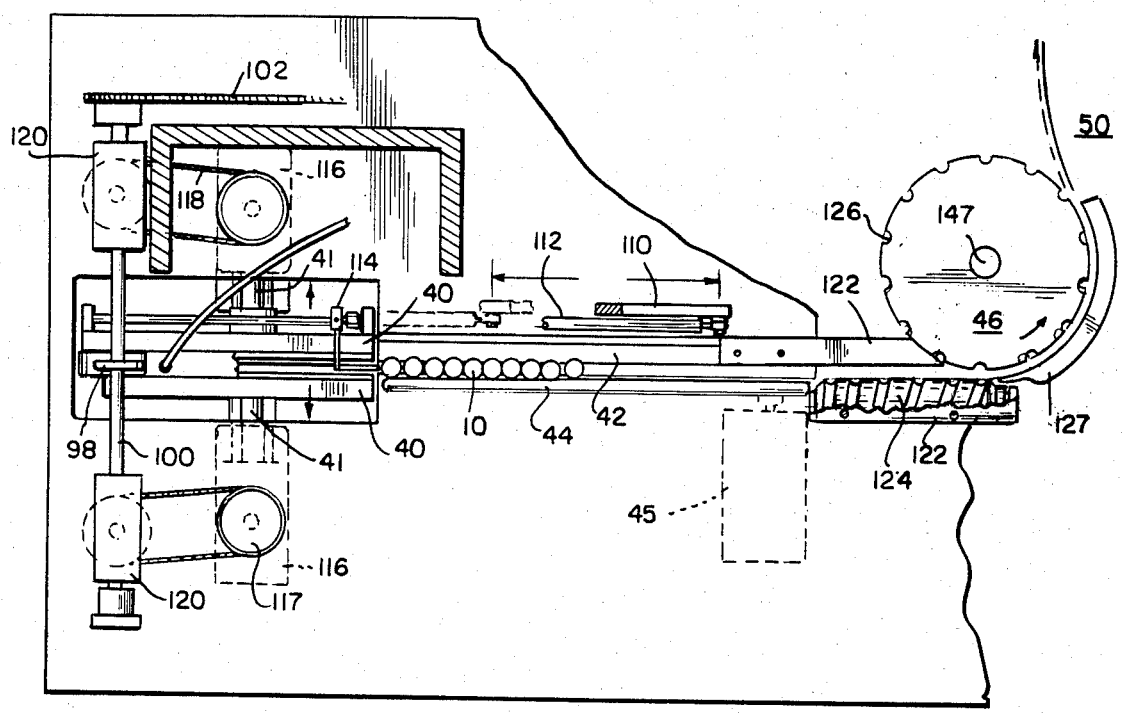
FIG. 6 is a plan view, with parts broken away, taken on the line 6—6 of FIG. 4.

As more fully shown in FIGS. 4, 5, and 6, the loading table 36 is mounted for sliding transverse movement on a pair of ways or bars 62 which themselves are mounted for movement longitudinally of the load carrier on a pair of bars 64 supported at level A of the machine. The table is driven transversely by a chain 66 secured to it by a connector 68 and strung around idler sprockets 70 coaxial with the longitudinal slide bars 64. The chain 66 is driven from a first motor 72 through a drive train which includes a gear box 74, but is connected to that drive train through an electromagnetic clutch 76 so that after a carrier plate has been unloaded, the table is released for manual movement to its loading position shown in full lines in FIG. 5. The pair of transverse bars 62 are connected by a link 78 to a jogger cam device 80 driven at half speed from the same drive train, for purposes of shifting the table longitudinally to align offset rows of syringes with the gang chuck.

The gang chuck 24 is mounted on a ram 82 carried by bars 84 which are reciprocated vertically by a cam box 86 mounted at level B of the machine. The cam box is driven through a sprocket 87 by a chain 88 from a vertical shaft 90 connected to the gear box 74 so as to be synchronized with the drive train from the motor 72.

The shaft 90 carries a cam 91 for actuating the air valve 25 which controls the air supply through the air line 89 to the gang chuck 24. The gang chuck 24 carries a stripper plate 92 which is biased to retracted position by springs 94 between the chuck 24 and a plate 96 which, in the raised position of the gang chuck 24, is in a position to be actuated by a stripper cam 98 on an elevated shaft 100. Such shaft 100 is driven by a chain 102 from a gear box 104 driven by the vertical shaft 90. That same gear box 104 is also connected by a chain 106 to drive a cam 108 which operates to retract a pusher arm 110. Such arm is mounted on a pivot 111 and is connected to a drive spring 115 which drives it through a forward stroke when permitted to do so by the cam 108. The lower end of the pusher arm 110 is connected by a link 112 to a pusher element 114 mounted on a slide bar carried with the rear retractable rail 40 and adapted to push along the rails 40 syringes 10 deposited thereon by the gang chuck 24. The pusher arm 110 is reciprocated through a pusher stroke in timed sequence with the other operations, and moves the syringe from the retractable rails 40 to the powered conveyor formed by the rail 42 and belt 44.

Figure 7:
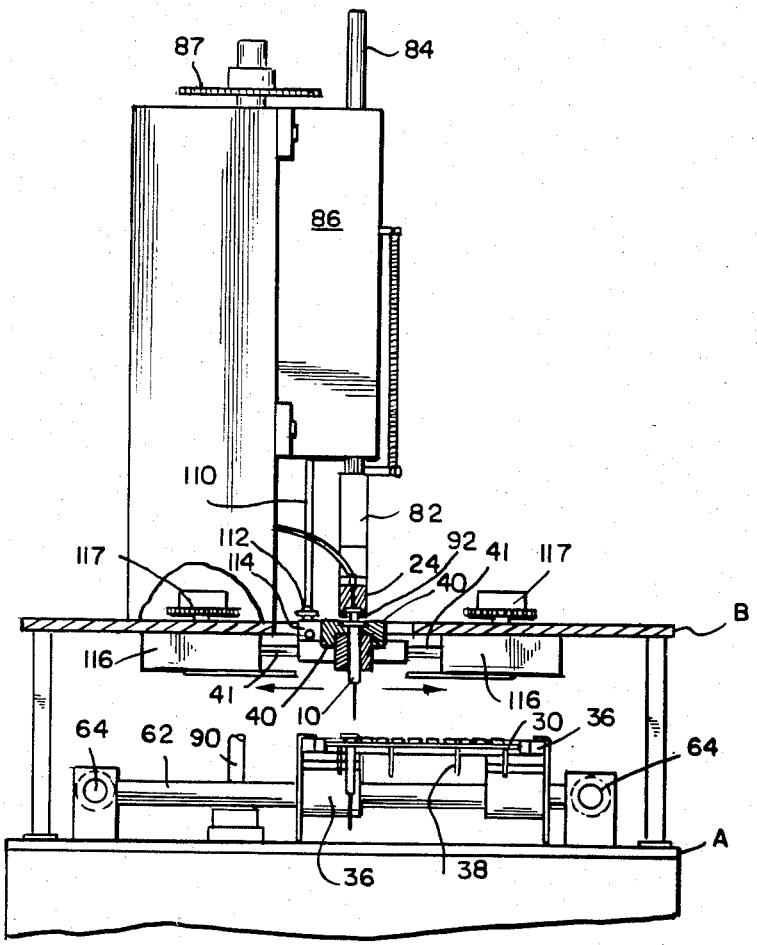
FIG. 7 is an end elevation of the loading mechanism shown in FIGS. 4-6.

As shown in FIGS. 6 and 7, the retractable rails 40 are carried by shafts 41 reciprocable in cam boxes 116 which are driven by chains 118 from gearboxes 120 driven by the elevated shaft 100. The cam boxes 116 are operative to retract the movable rails 40 from their closed positions shown in FIG. 7 to their open positions shown in FIG. 6 in timed sequence to permit the gang chuck 24 to move downward between them to pick up a row of syringes from the syringe carrier 30 on the loading table 36. When the row of syringes have been lifted, the cam boxes 116 then move the rails 40 to a closed position for supporting the syringes 10, air is cut off from the chuck, and the chuck then releases the syringes onto such rails. The stripper 92 acts to ensure such release.

When a row of ten syringes on the rails 40 have been moved by the pusher 114 onto the live conveyor 42-44, they are then continuously moved or urged forward by the continuous movement of the belt 44, which is driven by its own separate motor 45. The live conveyor 42-44 delivers the syringes to a pair of rails 122 which support the syringes for movement to the infeed star wheel 46. The syringes on such rails are fed to such star wheel and separated into spaced positions for transfer to such star wheel by a timing screw 124 driven in synchronism with the star wheel 46. The star wheel 46 includes a peripheral series of spaced seats 126 to receive syringes fed thereto from the rails 122 by the timing screw 124. Syringes transferred to the star wheel are held in the seats 126 by a guide bar 127 for delivery to the chucks carried by the turret 50.

Figure 8:
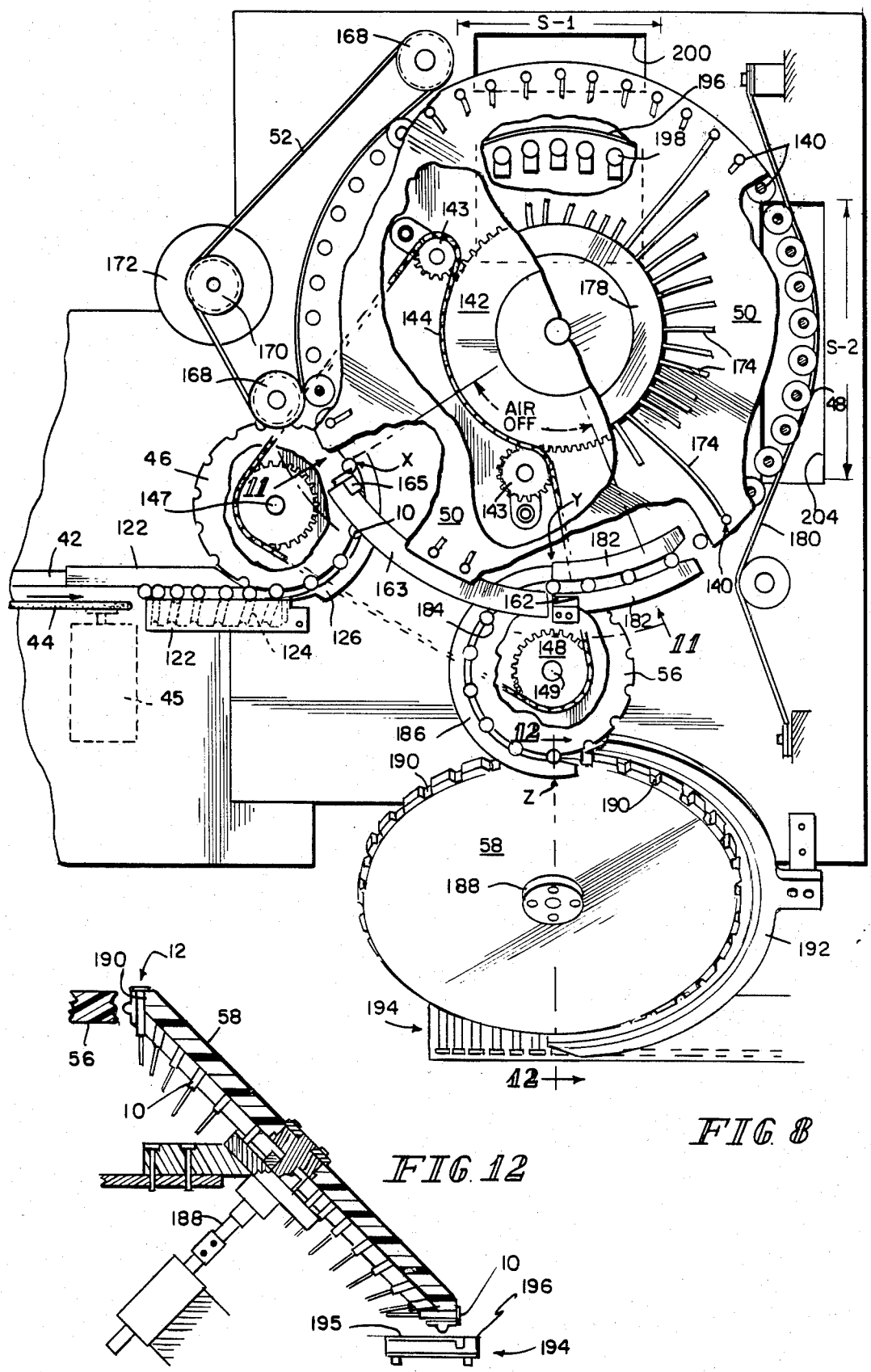
FIG. 8 is a plan view, with parts broken away, of the turret, the infeed and outfeed star transfer wheels, the spinner belt, and the angled delivery wheel which delivers the vertically disposed syringes to a horizontal outfeed conveyor.
Figure 9:
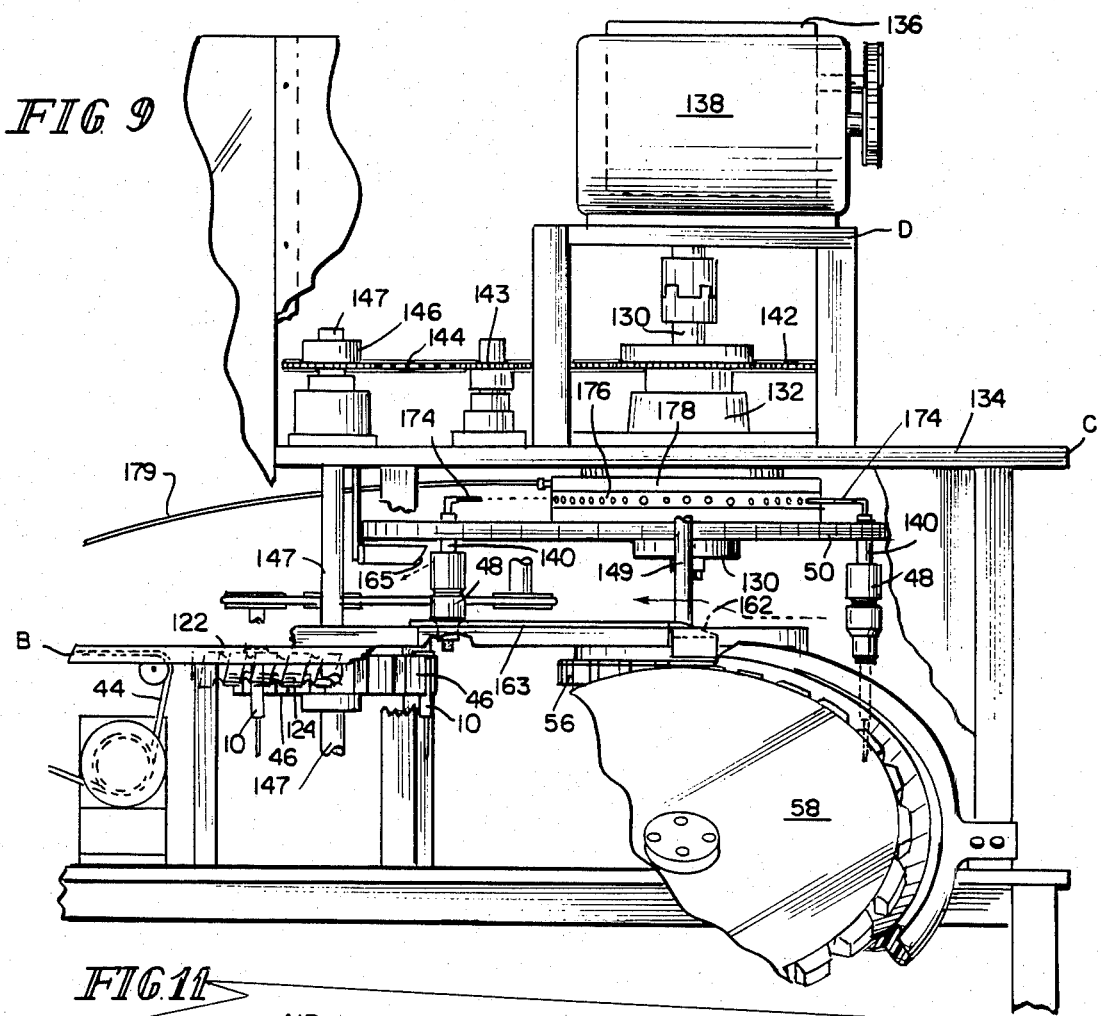
FIG. 9 is a front elevation of the apparatus shown in FIG. 8.
Figure 10:
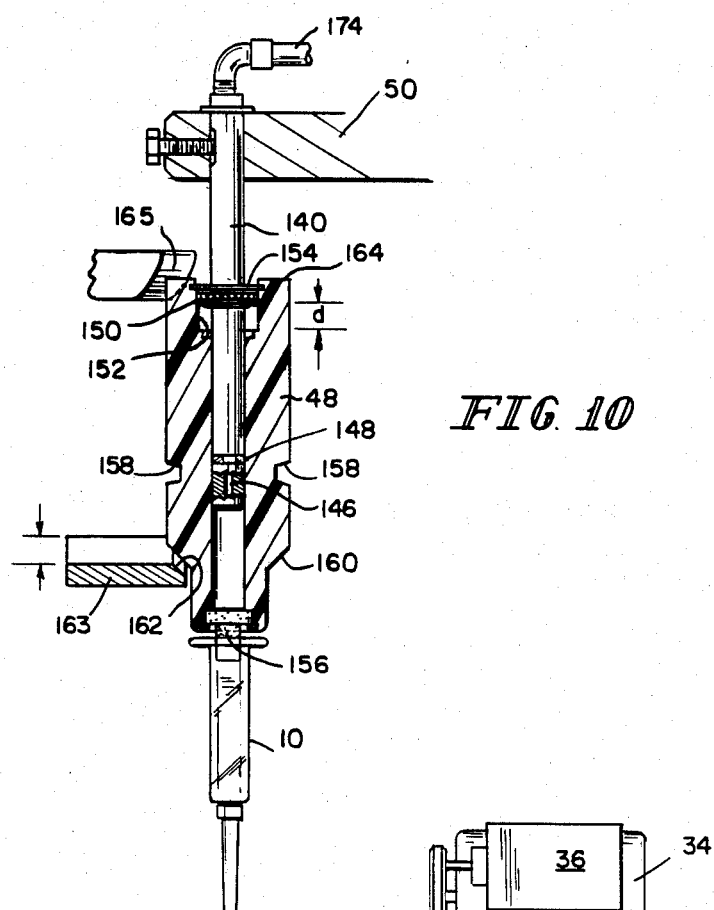
FIG. 10 is a vertical section showing a rotatable chuck and its mounting.

As shown in FIGS. 8-10, the turret 50 is in the form of a circular disk fixed to the lower end of a main shaft 130 mounted in a bearing 132 on a platform 134 at level C, above the level B of the conveyor mechanism and infeed star wheel 46 shown in FIGS. 4, 6, and 7. The drive shaft 130 is driven from above through a reduction gearbox 136 and second motor 138 mounted at level D on a platform elevated above the platform 134. The main shaft 130 carries a sprocket wheel 142 which is connected by a chain 144 to a drive sprocket 146 on the shaft 147 of the infeed star wheel 46 and to a sprocket 148 on the shaft 149 of the outfeed star wheel 56 so that such star wheels will be driven in timed sequence with the turret. The chain 144 is held in engagement with the drive sprocket 142 by idlers 143 in an arrangement which causes the star wheel shafts to rotate counterclockwise when the turret is driven clockwise as viewed in FIG. 8. The turret 50 includes a peripheral series of depending hollow spindle shafts 140 which in turn support the rotatable and axially movable chucks 48 which carry the syringes through the inspection path.

As shown in FIG. 10, each chuck 48 comprises a generally cylindrical body mounted in rotatable and vertically movable relation on a hollow spindle 140 fixed in the turret 50. The spindle contains an axial air passage 146 and is sealed to the spindle by an annular gasket 148. Air pressure will thrust the chuck downward. A thrust bearing 150 mounted on the spindle within a counterbore 152 in the upper end of the chuck body bears against a retaining ring 154 to limit downward movement of the chuck. The thrust bearing is of substantially shorter length than the counterbore 152 so that the chuck 48 is movable upward on the spindle 140 through a limited distance which provides sufficient axial movement of the chuck 48 to engage and disengage the chuck from the open ends of the syringes.

The bottom end of the chuck 48 carries an expansible insert 156, like the insert 26 on the gang chuck 24 as shown in FIG. 1, and is adapted to clutch the chuck to a syringe 10 to carry it through the inspection path. The chuck 48 is formed intermediate its length with a V groove 158 for the reception of the V-shaped spin belt 52. The chuck also has a conical lower face 160 adapted to engage a lift cam 162 for lifting the chuck 48 to disengage its expansible insert 156 from a syringe 10 at the end of the inspection path, and to ride in elevated position along a cam rail 163 as the chuck travels to the infeed transfer point at the start of the inspection path. Similarly, the chuck 48 has a top end face 164 adapted for engagement with a downthrust cam 165 shown diagrammatically in FIG. 10 to ensure downward movement of the chuck to engage its expansible insert in a syringe at the beginning of the inspection path. The cams 162 and 165 are more fully described below. As shown in FIG. 8, the spinner belt 52 is trained around a pair of angularly spaced idler pulleys 168 and the drive pulley 170 of an independent spin-drive motor 172.

As shown in FIGS. 8 and 9, the upper end of each chuck spindle 140 is connected by an air tube 174 to an individual valve pocket in a valve plate 176 which rides in sealed relation with a manifold 178 connected to a source of air under pressure as by an air line 179. The manifold is formed with an annular cavity of limited angular extent designed to supply air under pressure to the several valve pockets and thence to the spindles and the expandable inserts 156 of the chucks 48 during a predetermined angular movement of the turret 50 and to shut off air during the balance of such angular movement, as indicated in FIG. 8.

Figure 11:
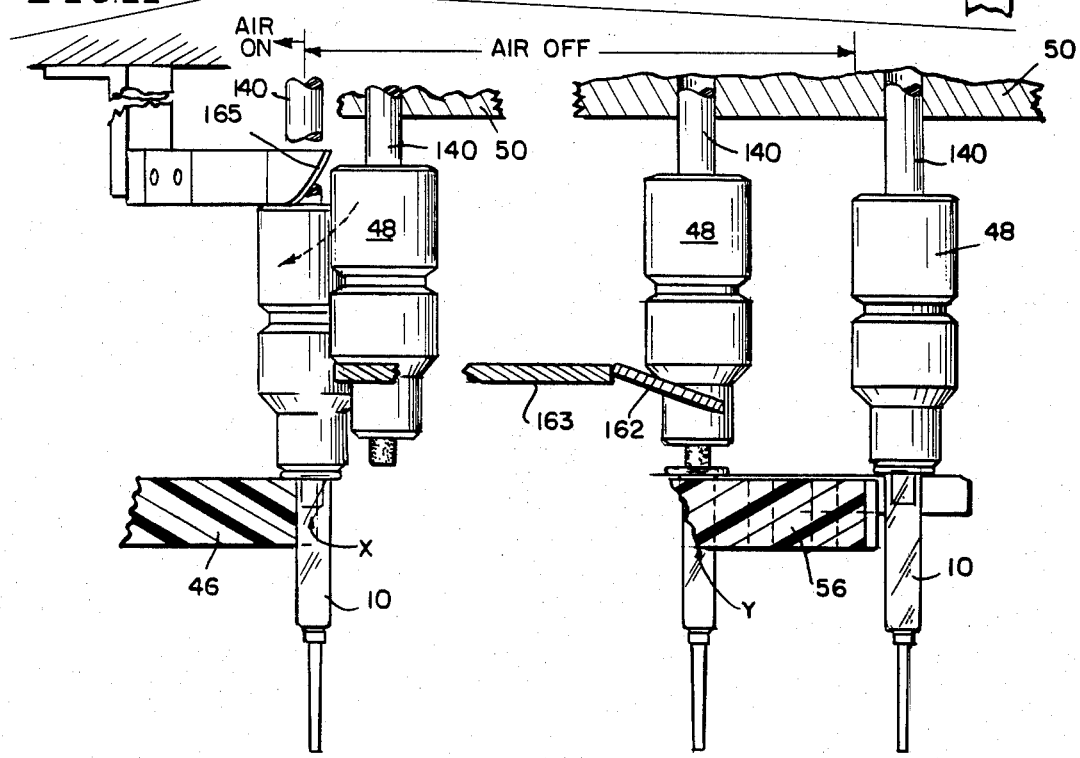
FIG. 11 is a view taken on the line 11—11 of FIG. 8 showing the cam and rail mechanism which lifts the rotary chucks out of engagement with the syringes at the outfeed star wheel and drops the chucks into engagement with the syringes at the infeed star wheel.

As shown in FIGS. 8 and 11, the cam rail 163 referred to in connection with FIG. 10 extends generally from the outfeed transfer point Y between the turret 50 and the outfeed star wheel 56 to the infeed transfer point X between the turret 50 and the infeed star wheel 46. Between these two transfer points, the cam rail 163 holds the chucks 48 in elevated position, so that their expandable inserts 156 are above the level of the upper ends of syringes 10 carried by the infeed star wheel 46. The infeed transfer point X between the infeed star wheel 46 and the turret 50 is substantially on a line connecting the axes of such star wheel and turret, where the path of syringes carried by the infeed star wheel 46 is tangent to and momentarily coincident with the path of the chucks 48 on the turret. At such point, the cam bar 163 is terminated so as to release each chuck 48 from its elevated position to allow the chuck to drop downward to engage its expansible insert 156 in the syringe 10 which is then positioned below the chuck by the infeed star wheel 46. The down thrust cam 165 is located at this point to ensure such downward movement of the chuck into engagement with the syringe. Air is then applied, and the syringe is then gripped by the chuck, with the chuck in its downmost position, and the syringe is thus transferred to the chuck to be carried thereby along the inspection path.

As shown in FIG. 8, movement of the turret 50 first carries the chucks 46, with syringes suspended thereon, into engagement with the spin belt 52 so that the chucks and syringes are rapidly spun as they move toward the first inspection station S-1. As they approach such station, they leave the belt 52, and friction then causes the chucks to stop rotating. This stops the spinning of the syringe bodies, but the liquid contained therein continues to spin so as to suspend solid particles for observation during the inspection.

From the first inspection station S-1, the chucks and their suspended syringes 10 are carried to the second inspection station S-2, where the chucks come into engagement with a stationary belt 180 which engages in the grooves 158 of the chucks and causes the chucks to roll along such belt and thereby to slowly rotate the suspended syringes 10 as they pass the second inspection station.

The turret then carries the chucks and their syringes to the outfeed transfer point Y for transfer to the outfeed star wheel 56. As they approach such star wheel, the syringes 10 move between a pair of exit rails 182 adapted to support them in further travel. The air supply to the chucks is then cut off, so that the inflatable inserts in the syringes deflate to release the syringes for separation from the chucks. The inserts remain in the chucks, however, to continue to move the syringes with the turret to the outfeed transfer point Y. At this point, the syringes become engaged in seats 184 in the outfeed star wheel 56, the exit rails 182 terminate, and the chucks come into engagement with the upward-sloping cam face 162 on the cam at the rail 163. Such upward cam 162 lifts the chucks on their spindles a distance d (FIG. 10) sufficient to disengage their deflated inserts 156 from the syringes so that the syringes are free to travel with the outfeed star wheel 56. The chucks continue to be held in elevated position by the rail 163 throughout their travel from the outfeed transfer point Y at the outfeed star wheel 56 to the infeed transfer point X at the infeed star wheel 46. The chucks then drop into infed syringes at the transfer point X at the start of the inspection path, as described above.

The syringes engaged in the seats 184 in the outfeed star wheel 56 are retained therein by a guide bar 186 so as to be carried in depending vertical positions through 180° of travel to a transfer point Z to the delivery wheel 58. As best seen in FIG. 12, such delivery wheel 58 is carried by a drive shaft 188 at a 45° angle, so that the wheel moves in a plane at an opposite 45° angle. The edge face of the delivery wheel 58 lies on a 90° cone and at 45° to the plane of the wheel. Such edge is formed with a series of pockets 190, spaced to receive the succession of syringes delivered thereto by the outfeed star wheel 56. The seats 190 are at a 45° angle to the plane of the 45° delivery wheel 58 so that they are vertically disposed at the transfer point Z and adapted to receive the syringes 10 in depending vertical position from the outfeed star wheel 56. The syringes transferred to the delivery wheel 58 are retained in the pockets 190 by a guide rail 192 extending through 180° about the delivery wheel. The angularly held syringes 10 are thus carried through 180° of travel in the delivery wheel, from their vertical positions at the top of such wheel to horizontal positions at the bottom of the wheel, as shown in FIG. 12. At this point, the rail 192 terminates, and the syringes drop out of the pockets 190 in the delivery wheel 58 onto an outfeed conveyor 194. Desirably, such conveyor is composed of a series of buckets 196 shaped to receive individual syringes and to support them in predetermined horizontal positions for conveyance to subsequent processing apparatus, such as rod-inserting or labeling apparatus.

Figure 13:
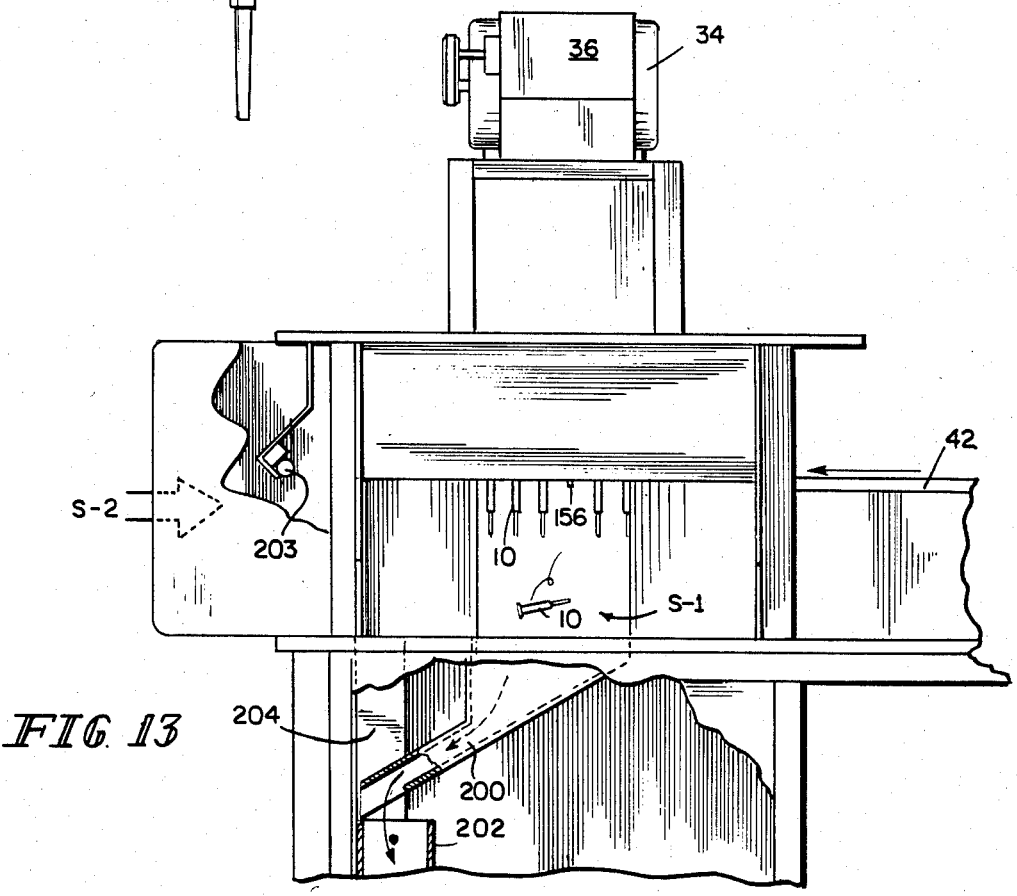
FIG. 13 is an elevation at the first inspection station.

As shown in FIGS. 8 and 13, at the first inspection station S-1, the syringes 10 are carried in depending position across a translucent screen 196 illuminated from behind by a series of fluorescent tubes 198 so as to be inspected against back lighting. As the syringes enter the inspection station, the syringes have left the spinning belt 52 and have stopped their rapid rotation, but their liquid contents 18 are still rotating sufficiently to suspend solid particles in the liquid so as to be observable in such back lighting. If the inspector observes the presence of such unwanted particles in any syringe, or any other defect, the defective syringe is manually pulled off the inflated insert of its supporting chuck and is dropped into a chute 200, leading to a reject box 202.

The second inspection station S-2 is similarly provided with a reject chute 204, shown in FIG. 8. At this station, the syringes are front-lighted, as by a light tube 203. The chucks roll along the stationary belt 180 so that they and their suspended syringes rotate slowly with the liquid content of the syringes quiescent. This permits the syringes to be observed from all sides for the detection of cracks, inadequate fill level, misshapen pistons, and other relatively gross defects. Both at this station and at the first inspection station A, the syringes are presented for inspection in a continously moving series of a plurality of closely spaced syringes so that a comparative inspection can be carried out to readily reveal particular syringes which differ markedly from other adjacent syringes in the series.

Operation of the loading section of the inspection apparatus is as follows: With such apparatus as shown in FIGS. 4–7 at rest, the drive train from the first motor 72 will be inactive, and the electromagnetic clutch 76 controlling the movements of the loading table 36 will be released so that such table is free for manual movement. The operator manually moves such table to the left to its loading position as shown in full lines in FIG. 5, and loads a syringe carrier 30 onto the supporting bars 38 of that table. In this position, the table will position the first row of syringes in the carrier in the same plane as and immediately below the inflatable inserts 26 of the gang chuck 24 carried by the ram 82, and the table will be in a position to close a limit switch 206 to condition the loading cycle to begin. The table 36 will also be longitudinally in its OUT position as shown in full lines in FIG. 5 so that the syringes in the first row of the carrier 30 will be aligned immediately below those inflatable inserts 26, as shown in FIG. 7. The rails 40 will be retracted, and the pusher 114 will be in its rearward position to the left as shown in FIG. 4. The operator then actuates a start button, and the loading operation proceeds as follows:

(1) The chuck ram and gang chuck 24 descends between the retracted rails 40 to engage the syringes of the first row.

(2) The cam 91 actuates the air valve 25 to supply air pressure to the gang chuck to inflate the inserts 26 to grip the syringes.

(3) The chuck ram then rises to lift the syringes to between the rails 40 (FIG. 4).

(4) The rails close to their conveyor position beneath the flanges 22 of the syringes (FIG. 7).

(5) The cam 91 actuates the valve 25 to cut off and vent the air pressure on the gang chuck so as to deflate the chuck inserts 26.

(6) The stripper cam 98 depresses the stripper 92 to ensure that the syringes are disengaged from the gang chuck 24 and dropped onto the closed rails 40.

(7) The pusher 114 linked to the pusher arm 110 is driven by the drive spring 115 through a forward stroke to move the syringes on the rails 40 forward onto the live conveyor formed by the rail 42 and the moving belt 44. Such conveyor then carries the syringes forward toward the infeed star wheel 46, and the pusher returns to its retracted position as shown in full lines in FIG. 4.

(8) The rails 40 are retracted so that they are again open for a new cycle.

(9) After the row of syringes has been elevated as in step (3) above, to clear the load table, the table drive chain 66 is actuated to step the load table 36 forward to bring the second row of syringes in the carrier 30 into the plane of the gang chuck 24.

(10) Concurrently, the table jogger mechanism 78-80 moves the table from its OUT position shown in full lines in FIG. 5 to its IN position shown in dotted lines, so as to align the syringes of that offset second row with the inflatable inserts 26 of the gang chuck 24.

(11) The mechanism then repeats the loading cycle of items 1-10 above to load the successive rows of syringes onto the conveyor rails 40 and thence to the live conveyor 42-44.

(12) During each successive cycle, the table 36 is advanced to bring the next row of 24, and is jogged between its IN and OUT positions to align the next successive rows of syringes with the inflatable inserts of the chuck.

The loading cycles as thus described are repeated until all ten rows of syringes in the carrier 30 have been removed therefrom and loaded onto the live conveyor 42-44. The table 36 in its final position for loading the tenth row of syringes engages a limit switch 208 which initiates a control cycle to cause the loading sequence to cease when that tenth row has been loaded onto the rails and thence onto the live conveyor 42-44. The clutch 76 controlling the drive to the loading table 36 then becomes disengaged and the operator then manually moves the table 36 back to its starting position where it conditions the limit switch 206 for a subsequent loading sequence, and the operator removes the unloaded carrier 30 and replaces it with a new carrier 30 containing a new lot of ten rows of ten syringes each. The loading sequence is then repeated. A continuous supply of syringes is thus supplied to the infeed live conveyor 42-44.

In the operation of the inspection portion of the apparatus, shown in FIGS. 8 and 9, the syringes 10 carried forward on the live conveyor 42-44 are fed in spaced relation by the timing screw 124 to the seats 126 of the infeed star wheel 46, which carries them to the infeed transfer point X. Chucks 48 on the turret there drop off the rail 163 to engage their inflatable inserts 156 in the syringes and the inserts are inflated to grip the syringes. The chucks then carry the syringes along the inspection path, first traveling along the spin belt 52 which drives the chucks to rapidly spin the syringes. The chucks then leave such belt and the syringe rotation stops while liquid in them continues to rotate to suspend solid particles as the syringes traverse the first inspection station. Defective syringes are manually removed from the chucks and dropped into the reject chute 200. The syringes on the chucks then are carried to the second inspection station S-2 where the chucks are rolled along the stationary belt 180 to cause the syringes to be slowly rotated as they pass in series through that inspection station. The syringes are then carried by the chucks to the exit rails 182, where the air is cut off from the inflatable inserts 156 to allow the syringes to be transferred at point Y to the outfeed star wheel 56 as the chucks are elevated out of engagement with the syringes by the cam 162. The star wheel 156 carries the syringes through 180° to a transfer point Z at which they are transferred to the pockets 190 of the angular delivery wheel 58 which carries and tilts them from a vertical position at the top of such wheel to a horizontal position at the bottom of such wheel. At that point, the syringes are dropped into the receiving cavities 195 of the buckets 196 of the outfeed conveyor 194.

What is claimed is:

1. Apparatus for loading onto processing mechanism filled hypodermic syringes or the like having a needle end and an opposite open end provided with a finger flange, comprising a movable loading table adapted to receive a syringe carrier containing a plurality of rows of syringes, each row containing a plurality of syringes, means to move said table stepwise to position said rows successively in a loading position, a feed conveyor having a pair of spaced longitudinal conveyor elements adapted to receive syringe bodies between them and to engage beneath the finger flanges of the syringes to support them in depending positions for longitudinal movement along the conveyor, a gang chuck having means for clutching a plurality of syringes in a row and means to move the same in synchronism with said table moving means to clutch a row of syringes at said loading position, to carry the syringes therefrom to the conveyor, and to release the same onto the conveyor.

2. Apparatus as in claim 1 in which said conveyor includes a pair of separable rails and means to move the same between a closed syringe-conveying position and an open chuck-clearing position, said table-moving means, chuck-moving means, and rail-moving means being operable in synchronism to position a row of syringes for chuck engagement and to open said rails, to move the chuck between the opened rails to clutch the row of syringes and lift them between the rails, and to close the rails to their syringe-conveying position, the chuck being then operated to release the syringes for support on the conveyor.

3. Apparatus as in claim 2 with the addition of an adjoining conveyor section having means to continuously move syringes therealong, and means to move the syringes along the rails and therefrom to said adjoining conveyor section.

4. Apparatus as in claim 3 in which said table is adapted to receive a carrier in which certain rows of syringes are offset from others, further comprising means for successively aligning the offset rows with the syringe-clutching elements of the gang clutch when such rows are presented in the loading position.

5. Apparatus as in claim 2 in which said-table is adapted to receive a carrier in which certain rows of syringes are offset from others, further comprising means for successively aligning the offset rows with the syringe-clutching elements of the gang clutch when such rows are presented in the loading position.

6. Apparatus as in claim 1 in which said table is adapted to receive a carrier in which certain rows of syringes are offset from others, further comprising means for successively aligning the offset rows with the syringe-clutching elements of the gang clutch when such rows are presented in the loading position.

7. Apparatus for loading onto processing mechanism filled hypodermic syringes or the like having a needle end and an opposite open end provided with a finger flange, comprising a support adapted to receive a syringe carrier containing a plurality of rows of syringes, each row containing a plurality of syringes, means to move said carrier stepwise to position said rows successively in a loading position, a feed conveyor having elements adapted to engage beneath the finger flanges of the syringes to support them in depending positions for longitudinal movement along the conveyor, a gang chuck having means for clutching a plurality of syringes in a row and means to move the same in synchronism with said carrier moving means to clutch a row of syringes at said loading position, to carry the syringes therefrom to the conveyor, and to release the same onto the conveyor.

8. Apparatus as in claim 7 in which said conveyor includes a pair of separable rails and means to move the same between a closed syringe-conveying position and an open chuck-clearing position, said carrier means, chuck-moving means, and ail-moving means being operable in synchronism to position a row of syringes for chuck engagement and to open said rails, to move the chuck between the opened rails to clutch the row of syringes and lift them between the rails, and to close the rails to their syringe-conveying position, the chuck being then operated to release the syringes for support on the conveyor.

9. Apparatus as in claim 8 with the addition of an adjoining conveyor section having means to continuously move syringes therealong, and means to move the syringes along the rails and therefrom to said adjoining conveyor section.

* * * * *

UNITED STATES PATENT AND TRADEMARK OFFICE
CERTIFICATE OF CORRECTION

PATENT NO. : 4,500,247
DATED : February 19, 1985
INVENTOR(S) : Hugh P. McKnight et al It is certified that error appears in the above-identified patent and that said Letters Patent is hereby corrected as shown below:

Column 12, line 17 (claim 8), change "ail-moving" to --rail-moving--.

Signed and Sealed this

First Day of October 1985

[SEAL]

Attest:

DONALD J. QUIGG

Attesting Officer

Commissioner of Patents and Trademarks—Designate